United States Patent [19]

Horiguchi et al.

[11] Patent Number: 5,874,624
[45] Date of Patent: Feb. 23, 1999

[54] PROCESS FOR THE PREPARATION OF A DIHYDROXYAMINO COMPOUND

[75] Inventors: Akira Horiguchi, Ohtake; Akihisa Takabe, Himeji; Etsuo Takemoto, Hiroshima-ken, all of Japan

[73] Assignee: Daicel Chemical Industries, Ltd., Sakai, Japan

[21] Appl. No.: 954,921

[22] Filed: Oct. 21, 1997

[30] Foreign Application Priority Data

Oct. 23, 1996 [JP] Japan ................................. 8-299546
Nov. 22, 1996 [JP] Japan ................................. 8-327902
Sep. 24, 1997 [JP] Japan ................................. 9-276488
Sep. 24, 1997 [JP] Japan ................................. 9-276489

[51] Int. Cl.$^6$ ................................. C07C 209/84
[52] U.S. Cl. ........................ 564/475; 564/476; 564/497
[58] Field of Search ................... 564/497, 475, 564/476

[56] References Cited

U.S. PATENT DOCUMENTS 5,750,792  5/1998  Koyama et al. ........................ 564/507

*Primary Examiner*—Brian M. Burn
*Attorney, Agent, or Firm*—Morgan & Finnegan, LLP

[57] ABSTRACT

Disclosed are a process for the preparation of a dihydroxyamino compound in which water and discoloring ingredients are removed while preventing decomposition of a dihydroxyamino compound by distilling a crude reaction liquid containing an epoxy compound and an amino compound at a specified temperature and pressure, a process for improving a yield of a dihydroxyamino compound having high purity by recirculating an aqueous solution of an amino compound recollected from a crude reaction liquid into a reaction step, and a process in which there are prevented discoloration and a yield decline of a dihydroxyamino compound.

20 Claims, No Drawings

PROCESS FOR THE PREPARATION OF A DIHYDROXYAMINO COMPOUND

FIELD OF THE INVENTION

The present invention relates to a process for the preparation of a dihydroxyamino compound. In more detail, the present invention relates to processes in which water and discoloring ingredients are removed from a crude reaction liquid by distillation at a specified temperature and pressure while preventing decomposition of a dihydroxyamino compound, in which a yield of the dihydroxyamino compound is improved by recirculating a solution of an amino compound recollected from the crude reaction liquid, and in which a crude dihydroxyamino compound is fed into a specified position in a distillation column, and further, in which high-boiling-point ingredients are separated through two-stages distillation.

BACKGROUND OF THE INVENTION

A dihydroxyamino compound is industrially useful and, for example, 1-amino-2,3-propanediol which is one of the dihydroxyamino amino compound is an industrially interesting product as a starting material for a non-ionic X-ray contrast agent (for example, Belgian Pat. No. 855,580), and the demand thereof recently has increased.

For example, JP-A-62230754 (corresponding to U.S. Pat. No. 5,023,379 or DE3609978) discloses a process for the preparation of 1-amino-2,3-propanediol by way of an amine compound from glyceryl aldehyde and ammonia. Further, Swiss patent CH 253256 discloses a process for the preparation of 1-amino-2,3-propanediol by way of an imide compound from acetone-alpha-chlorohydrin and ammonia. Still further, "M. Fedoronko et al., Electroreduction of triose oximes, Chem. Papers 43(2), 335 to 341 (1989)" discloses a process for the preparation of 1-amino-2,3-propanediol by an electroreduction method.

In the processes, it is theoretically thought that 2-amino-1,3-propanediol is not absolutely produced as a by-product, and the processes do not state it at all.

However, until now, the processes have not been industrially put into practice because of high costs in starting raw materials and complicated processes.

Therefore, at present time, 1-amino-2,3-propanediol has typically been industrially produced by a reaction of glycidol or an epihalohydrin with ammonia.

A process for the preparation of 1-amino-2,3-propanediol produced by a reaction of glycidol or an epihalohydrin with ammonia is disclosed in, for example, "Ber. Deutsche Chem. Ges.", Vol. 32, pages 750–757, 1899 (L. Knorr et al) and "Journal of Organic Chemistry", Vol. 27, pages 2231–2233, 1962 (K. Baum et al) and, further, JP-A-56161355 (corresponding to U.S. Pat. No. 4,358,615), JP-A-56161356 (corresponding to U.S. Pat. No. 4,356,323), JP-A-56161357 (corresponding to U.S. Pat. No. 4,360,697), JP-A-04352748 (corresponding to U.S. Pat. No. 5,556,576 or EP 0470004), JP-A-03041056, JP-A-03041057, JP-A-03063251, JP-A-03086851, and JP-A-08012628, etc.

In the processes by the reaction of glycidol or the epihalohydrin with ammonia, it is thought that a reaction mechanism is a ring-opening addition reaction to epoxy group by attack in which electron pair in nitrogen atom of ammonia attacks a carbon atom in epoxy group which is short in electron.

In the processes, 2-amino-1,3-propanediol which is unpreferred for 1-amino-2,3-propanediol is by-produced by a side reaction that ammonia attacks the second carbon from the terminal without an attack to the carbon at the terminal, and impurities such as bis (2,3-dihydroxypropyl) amine are produced by a reaction of 1-amino-2,3-propanediol with glycidol. It is difficult to avoid the side reaction in view of characteristics in the reaction.

It is to be noted that in the processes by the reaction of the epihalohydrin with ammonia, the epihalohydrin produces glycidol in a reaction step of the process.

In the processes described in the above publications, an exceedingly large amount of ammonia is employed in order to increase an yield of 1-amino-2,3-propanediol. A recently commercially supplied 1-amino-2,3-propanediol contains 0.3–0.5% by weight of 2-amino-1,3-propanediol as impurities which are unpreferred in a succeeding step.

However, JP-A-56161355, JP-A-56161356, and JP-A-56161357, JP-A-03063251, JP-A-03041056, JP-A-03041057, and JP-A-03086851 do not specifically state a separation of 2-amino-1,3-propanediol at all.

In the JP-A-04352748 (corresponding to U.S. Pat. No. 5,556,576 or EP 0470004), there is disclosed a process for the preparation of 1-amino-2,3-propanediol containing less than 0.3% by weight of 2-amino-1,3-propanediol by a continuous distillation of a crude liquid of 1-amino-2,3-propanediol with a distillation column equipped with a packing having low pressure loss and a thin-layer evaporator or a scraping-type thin layer evaporator, as a result of finding that 2-amino-1,3-propanediol has, though exceedingly slight, higher boiling point than 1-amino-2,3-propanediol.

However, it is desired that 1-amino-2,3-propanediol is more efficiently separated in the process from a viewpoint of apparatuses, efficiency in using raw materials, and quality of a product.

Further, the JP-A-08012628 proposes that distillation is carried out with a batchwise distillation equipment while streaming an inert gas. However, since 1-amino-2,3-propanediol is thermally unstable, it is not thought that the batchwise distillation is more advantageous than a continuous distillation because of a long holding time of period.

In the circumstances, there has been desired a process in which the content of 2-amino-1,3-propanediol in 1-amino-2,3-propanediol can be efficiently decreased to less than 0.3% by weight.

In the above-mentioned reaction, since the exceedingly large amount of the amino compound is employed in a state of an aqueous solution in order to improve a yield of 1-amino-2,3-propanediol, a large amount of ammonia and water are unavoidably contained in a crude reaction liquid.

Further, discoloring ingredients are readily produced by side reactions in a step for removing ammonia and water from the crude reaction liquid.

JP-A-03086851 discloses that temperature at a bottom portion of an evaporator is controlled in a specified range, and holding time of period is controlled within 1 hour in a reduced distillation step when refined, whereby, there is improved discoloration in a dihydroxyamino compound which is a desired product.

In the processes, refining conditions are limited, and it is difficult to obtain a sufficient yield.

Still further, there is not detailedly described a method for removing discoloring ingredients. Particularly, in the case that the dihydroxyamino compound is employed as a raw material for an X-ray contrast agent, discoloration degree and water content become problematic.

In general, the discoloration degree is roughly controlled in less than 50 of APHA as a target value, and water content is roughly controlled in less than 0.2% by weight as a target value.

However, as described above, there has not been known a method for improving a color hue and water content.

In the situations, there has been desired a development of a method for refining a dihydroxyamino compound without discoloration from a crude reaction liquid.

Also, there are industrially important an improvement in yield of the dihydroxyamino compound and effective recollection and recirculation of unreacted amino compound.

JP-A-03063251 discloses that an ammonia aqueous solution is employed as an amino compound, however, there is not detailedly described recollection of unreacted ammonia. In the processes described in JP-A-56161355, JP-A-56161356, and JP-A-56161357, ammonia is employed as an amino compound, and liquefied ammonia is employed in place of an ammonia aqueous solution in order to reduce the volume of ammonia.

Accordingly, in order to recirculate ammonia into a reaction system, unreacted ammonia must be recollected as liquefied ammonia or as an aqueous solution through a scrubber, etc.

Boiling point of ammonia is −34° C. at ordinary pressure, and in order to recollect ammonia by distillation, temperature of a coolant must be adjusted to less than the boiling point of ammonia, whereby, plant costs and running costs increase, resulting in that it is unpreferred from viewpoint of economy.

Further, there is also thought a process in which distillation is carried out under pressurization in order to elevate the boiling point of ammonia and to elevate the temperature of the coolant.

However, the process requires a distillation column which can resist pressurization, unpreferably resulting in that plant costs increase, and the process requires an apparatus for storing liquefied ammonia.

Still further, in the process for recollecting distilled ammonia as an aqueous solution through a scrubber, etc., recollected ammonia must be converted from an aqueous solution into liquefied ammonia in order to recirculate into a reaction step, unpreferably resulting in that plant costs and running costs become considerably high.

In the circumstances, there has been desired a development of a process in which an amino compound is efficiently recollected from a crude reaction liquid, and recollected amino compound can be recirculated without any special treatments, resulting in that a dihydroxyamino compound can be efficiently prepared.

In addition, JP-A-56161355, JP-A-56161356, JP-A-56161357, JP-A-03041056, and JP-A-03041057 do not state color hue in the dihydroxyamino compound which is a product at all.

In the circumstances, there has been desired a development of a process in which a colorless dihydroxyamino compound is efficiently prepared from a crude liquid after removing low-boiling-point ingredients such as an unreacted amino compound and water from a crude reaction liquid.

The present invention aims at providing a process for efficiently preparing a dihydroxyamino compound in which discoloration is prevented. As a target discoloration value, it is important that an APHA value is less than 50.

SUMMARY OF THE INVENTION

An object of the present invention is an improved process for the preparation of a dihydroxyamino compound in which there are prevented discoloration and a yield decline of the dihydroxyamino compound.

A first aspect of the present invention is a process for the preparation of a dihydroxyamino compound characterized in that a crude reaction liquid containing a dihydroxyamino compound represented by general formula (1);

(in the formula, $R^1$–$R^7$ are a substituted group which includes any one of a hydrogen atom, an alkyl group, an alkenyl group, and an alkoxy group, respectively) is distilled in a column-top pressure of 0.1–30 Torr and a temperature of 60°–200° C., and then distilled vapor is cooled at a temperature of 40°–180° C., said dihydroxyamino compound is separated from water and low-boiling-point ingredients, and water content is adjusted to not more than 0.2% in said dihydroxyamino compound.

A second aspect of the present invention is a process for the preparation of 1-amino-2,3-propanediol characterized in that there is employed a distillation column equipped with a packing having pressure loss of not more than 0.5 torr per 1 theoretical plate at an upper side and a lower side of a feeding position, in the case that 1-amino-2,3-propanediol is obtained as a distillate by separation of a mixed liquid primarily containing 1-amino-2,3-propanediol and containing 2-amino-1,3-propanediol which is a by-product, water, and high-boiling-point ingredients with a distillation column.

A third aspect of the present invention is a process for the preparation of a dihydroxyamino compound represented by general formula (1),

(in the formula, $R^1$–$R^7$ are a substituted group which includes any one of a hydrogen atom, an alkyl group, an alkenyl group, and an alkoxy group, respectively) produced by the reaction of an epoxy compound represented by general formula (2),

(in the formula, $R^1$–$R^5$ are a substituted group which includes any one of a hydrogen atom, an alkyl group, an alkenyl group, and an alkoxy group, respectively, and $R^8$ is a hydroxyl group or a halogen atom) with an aqueous solution of an amino compound represented by general formula (3),

(in the formula, $R^6$ and $R^7$ are a substituted group which includes any one of a hydrogen atom, an alkyl group, an alkenyl group, and an alkoxy group, respectively), the improvement characterized in that an unreacted amino compound is recollected from a crude reaction solution containing said dihydroxyamino compound and said amino compound as a solution containing 5–80% by weight of said amino compound by evaporation, and then said solution is recirculated into a reaction system.

A fourth aspect of the present invention is a process for the preparation of a dihydroxyamino compound composed of the steps; distilling a crude liquid in which an unreacted amino compound and low-boiling-point ingredients are removed from a crude reaction liquid containing a dihydroxyamino compound represented by general formula (1) produced by the reaction of an epoxy compound represented by general formula (2) with an amino compound represented by general formula (3), and separating the dihydroxyamino compound from said low-boiling-point ingredients, the improvement characterized in that high-boiling-point ingredients are taken out of a bottom of an evaporator in a low concentration state containing not less than 20% by weight of said dihydroxyamino compound, and said dihydroxyamino compound is recollected by evaporation with an evaporator,

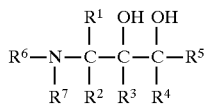
(1)

(in the formula, $R^1$–$R^7$ are a substituted group which includes any one of a hydrogen atom, an alkyl group, an alkenyl group, and an alkoxy group, respectively)

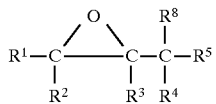
(2)

(in the formula, $R^1$–$R^5$ are a substituted group which includes any one of a hydrogen atom, an alkyl group, an alkenyl group, and an alkoxy group, respectively, and $R^8$ is a hydroxyl group or a halogen atom)

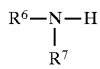
(3)

(in the formula, $R^6$ and $R^7$ are a substituted group which includes any one of a hydrogen atom, an alkyl group, an alkenyl group, and an alkoxy group, respectively).

DETAILED DESCRIPTION OF THE INVENTION

Hereinafter, the present invention is described in more detail.

According to a first aspect of the present invention, there is provided a process for the preparation of a dihydroxyamino compound characterized in that a crude reaction liquid containing a dihydroxyamino compound represented by general formula (1);

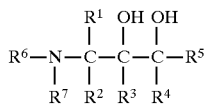
(1)

(in the formula, $R^1$–$R^7$ are a substituted group which includes any one of a hydrogen atom, an alkyl group, an alkenyl group, and an alkoxy group, respectively) is distilled in column-top pressure of 0.1–30 torr and a temperature of 60°–200° C., distilled vapor is cooled at a temperature of 40°–180° C., said dihydroxyamino compound is separated from water and low-boiling-point ingredients, and water content is adjusted to not more than 0.2% in said dihydroxyamino compound.

The dihydroxyamino compound in the present invention is a dihydroxyamino compound represented by the above-mentioned general formula (1).

In the formula (1), $R^1$–$R^7$ are a hydrogen atom or a substituted group which includes an alkyl group, an alkenyl group, an alkoxy group, respectively. In the substituted group, a carbon number is preferably 1–10, and more preferably 1–8.

The dihydroxyamino compound specifically includes 1-amino-2,3-propanediol, 1-amino-2,3-butanediol, 2-amino-3,4-butanediol, 1-amino-2,3-hexanediol, 1-monomethylamino-2,3-propanediol, 1-monoethylamino-2,3-propanediol, 1-monopropylamino-2,3-propanediol, 1,1-dimethylamino-2,3-propanediol, 1,1-diethylamino-2,3-propanediol, and 1,1-dipropylamino-2,3-propanediol, in which $R^1$–$R^5$ are a hydrogen atom or the alkyl group, respectively, 1-amino-2,3-pentanediol-4-en, 1-amino-2,3-hexanediol-4-en, 1-monoethylamino-2,3-hexanediol-4-en, and 1-diethylamino-2,3-hexanediol-4-en, in which any of $R^1$–$R^5$ includes the alkenyl group, respectively, and 1-amino-4-methoxy-2,3-butanediol, 1-monomethylamino-4-methoxy-2,3-butanediol, and 1,1-dimethylamino-4-methoxy-2,3-buanediol, in which any of $R^1$–$R^5$ includes the alkoxy group, respectively.

A crude reaction liquid in the present invention is a crude reaction liquid in a reaction step for preparing the dihydroxyamino compound by a reaction of an epoxy compound with an amino compound.

The epoxy compound is an epoxy compound represented by the above-mentioned general formula (2).

In the formula (2), $R^1$–$R^5$ are a hydrogen atom or a substituted group which includes an alkyl group, an alkenyl group, and an alkoxy group, respectively. $R^8$ is a substituted group which includes a hydroxyl group or a halogen atom, respectively. In the substituted group, a carbon number is preferably 1–10, and more preferably 1–8.

The epoxy compound specifically includes glycidol, 1,2-epoxy-3-butanol, 2,3-epoxy-1-butanol, 1,2-epoxy-3-pentanol, 1,2-epoxy-3-hexanol, 1,2-epoxy-3-heptanol, 3,4-epoxy-3-pentanol, 3,4-epoxy-4-methyl-2-pentanol, and 1,2-epoxy-3-decanol, etc., in which $R^1$–$R^5$ are a hydrogen atom or the alkyl group, respectively, 4,5-epoxy-3-hydroxy-1-pentene, 5,6-epoxy-4-hydroxy-2-heptene, 5,6-epoxy-4-hydroxy-6-methyl-2-heptene, and 5,6-epoxy-4-hydroxy-6-methyl-2-dekene, etc., in which any of $R^1$–$R^5$ includes the alkenyl group, respectively, and 4-methoxy-1,2-epoxy-3-hydroxybutane, 4-ethoxy-1,2-epoxy-3-hydroxybutane, and 6-ethoxy-3,4-epoxy-5-hydroxypentane, etc., in which any of $R^1$–$R^5$ includes the alkoxy group, respectively, or a compound containing a halogen such as epichlorohydrin in which $R^8$ is a chlorine atom.

The amino compound is an amino compound represented by the above-mentioned general formula (3).

In the formula (1), $R^6$ and $R^7$ are a hydrogen atom or a substituted group which includes an alkyl group, an alkenyl group, and an alkoxy group, respectively. In the substituted group, a carbon number is preferably 1–10, and more preferably 1–8.

The amino compound specifically includes a primary amine such as ammonia, monomethylamine, monoethylamine, mono-n-propylamine, monoisopropylamine, and monobutylamine, a secondary amine such as dimethylamine, diethylamine, di-n-propylamine, N-ethylmethylamine, and N-butylethylamine, a compound having an alkenyl group such as N-ethyl-2-methylallylamine, a compound having an alkoxy group such as monomethoxyamine, methylethoxyamine, ethylbutoxyamine, dimethoxyamine, and dibutoxyamine.

Molar ratio of the above-mentioned amino compound with respect to the above-mentioned epoxy compound is 2–100 mol, and preferably 3–50 mol based on 1 mol of the epoxy compound in order to improve a yield of the dihydroxyamino compound.

In the case of less than 2 mol, the yield of the dihydroxyamino compound becomes unpreferably worse, and in the case of exceeding 100 mol, the crude reaction liquid unpreferably increases, space-time-yield unpreferably lowers, water to be removed increases, and the yield of the dihydroxyamino compound does not unpreferably increase compared to the use amount of the amino compound.

The crude reaction liquid to be employed for distillation contains the dihydroxyamino compound in a proportion of 5–80% by weight, and preferably 10–70% by weight.

If the dihydroxyamino compound is in the range, discoloring ingredients and water can be removed while preventing decomposition of the dihydroxyamino compound.

For example, in the case that the dihydroxyamino compound is 1-amino-2,3-propanediol, 1-amino-2,3-propanediol concentration is preferably 30–99% by weight in the crude reaction liquid, and there are contained high-boiling-point ingredients such as di(hydroxypropyl)amine in which 1-amino-2,3-propanediol further reacts to glycidol, and a slight amount of low-boiling-point discoloring ingredients in the crude reaction liquid.

In the processes for the preparation of the dihydroxyamino compound in the present invention, distillation apparatuses are not particularly limited in a style if deterioration by heating can be prevented, and there can be employed a distillation apparatus composed of an evaporating portion and a distillation column.

As the evaporating portion, there may be employed any of, for example, a natural circulation evaporator, a forcibly-circulating thin layer evaporator and a liquid-film type evaporator, which are classified in "Kagaku Kogaku Tsuron I" (edited by Haruo Hikita, the third edition, page 90, 1971, published by Asakura Shoten, in Japan), can unlimitedly be used. Of them, a liquid-film type evaporator, in which the holding time of a liquid is short, is preferably be employed. Particularly, a wiped film evaporator is preferably employed because it is capable of preventing a decrease of heat transfer efficiency even in the case of relatively highly viscous liquids, for example, the dihydroxyamino compound itself and the crude solutions thereof containing other components with higher boiling points.

As the distillation column, there is preferably employed a packed column having low pressure loss.

Further, distillation method by a batchwise process is more unpreferred than a continuous distillation method because of a long holding time of period of the dihydroxyamino compound in the distillation apparatus so much.

It is to be noted that the distillation apparatus in which a distillation column is combined with an evaporating portion having evaporating ability.

Pressures, temperatures at a column-top portion in the distillation apparatus, and cooling temperatures, that is, condensing temperatures are decided depending upon the concentration and thermal stability of the dihydroxyamino compound contained in the crude reaction liquid, the concentration and boiling points of the other ingredients, separability from the dihydroxyamino compound, reactivity, and thermal stability.

In the present invention, in the case that there is employed a distillation apparatus composed of a distillation column and an evaporating portion, temperatures in the evaporating portion are preferably 60°–200° C., particularly, 70°–190° C. In the case that the temperature in the evaporating portion is lower than 60° C., viscosity in liquid is too high, and distilling operation occasionally becomes unpreferably difficult.

On the other hand, in the case that the temperature in the evaporating portion exceeds 200° C., a distillate which is a product readily discolors by heat deterioration, and it unpreferably requires a heating means being capable of supplying high temperature.

Temperatures in the distillation column are 50°–180° C., and preferably 55°–75° C. If the temperatures are in the range, low-boiling-point ingredients and water can be efficiently removed by distillation while preventing decomposition of the dihydroxyamino compound.

Pressure in the evaporator is 0.1–50 Torr, and preferably 0.5–40 Torr. In the case that the pressure is less than 0.1 Torr, temperature in the evaporator becomes too lower, although thermal deterioration of the dihydroxyamino compound can be prevented, it is not practical because it requires a high price vacuum unit in order to maintain a super high vacuum state.

On the other hand, in the case that it exceeds 50 Torr, temperature elevates in the evaporator, whereby, the dihydroxyamino compound readily causes thermal deterioration, unpreferably resulting in causing discoloration of the dihydroxyamino compound by decomposition.

Pressure at a column-top of the distillation is 0.1–30 Torr, and preferably 0.2–20 Torr. If the pressure is in the range, low-boiling-point ingredients and water can be efficiently removed by distillation while preventing decomposition of the dihydroxyamino compound.

Vapor distilled out of the distillation column is preferably cooled in a temperature range of 40°–180° C., preferably 50°–170° C. Specifically, vapor distilled out is introduced into a condenser while controlling the temperature. In the case that the temperature for partially condensing is less than 40° C., low-boiling-point ingredients and water contained in the crude reaction liquid are also condensed together with the dihydroxyamino compound.

For that reason, low-boiling-point ingredients and water are mixed into the dihydroxyamino compound, whereby, a product discolors and water content increases in the product. On the other hand, in the case of exceeding 180° C., although the low-boiling-point ingredients and water are distilled out, the dihydroxyamino compound cannot be condensed in the condenser, unpreferably resulting in that yield of the dihydroxyamino compound becomes worse.

The distillation apparatus for preparing the dihydroxyamino compound may be one unit or a plurality of units.

Although there is thought a method for separating the low-boiling-point ingredients and water by a plurality of distillation apparatuses, an increase of the distillation apparatuses unpreferably results in an increase of costs in a plant and a complicated operation.

In the process for the preparation of the dihydroxyamino compound of the present invention, the dihydroxyamino compound is recollected in a condensate cooled in the condenser from vapor distilled out of the distillation column.

On the other hand, the low-boiling-point ingredients and water contained in the crude reaction liquid are partially recirculated into the distillation column in a vapor state after separating from the condensate, whereby, there can be obtained the dihydroxyamino compound having the water content of not more than 0.2% by weight, preferably not more than 0.15% by weight.

The dihydroxyamino compound obtained in the first aspect of the present invention has not more than 50 of APHA value which is a value of a color hue, preferably not more than 45, and more preferably not more than 40.

The dihydroxyamino compound having the APHA value has an advantage that a yield is improved in a succeeding step.

According to a second aspect of the present invention, there is provided a process for the preparation of 1-amino-2,3-propanediol characterized in that there is employed a distillation column equipped with a packing having pressure loss of not more than 0.5 torr per 1 theoretical plate at an upper side and a lower side of a feeding position, in the case that 1-amino-2,3-propanediol is obtained as a distillate by separation of a mixed liquid primarily containing 1-amino-2,3-propanediol and containing 2-amino-1,3-propanediol which is a by-product, water, and high-boiling-point ingredients with a distillation column.

The mixed liquid to be employed in the second aspect contains 1-amino-2,3-propanediol which is a primary compound, and 2-amino-1,3-propanediol which is a by-product, water, high-boiling-point ingredients, which includes a crude reaction liquid of glycidol with ammonia and a liquid in which low-boiling-point ingredients and water are removed from the crude reaction liquid, and further a mixture in which the above-mentioned substances are merely mixed.

In the present invention, 1-amino-2,3-propanediol is prepared by the reaction of glycidol with ammonia according to the reaction scheme as described below.

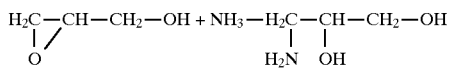

In the case of the preparation of 1-amino-2,3-propanediol by the reaction of epichlorohydrin which is one of epihalohydrins with ammonia, in which epichlorohydrin is firstly hydrolyzed by water to produce 3-chloro-1,2-propanediol, and then glycidol is produced through a cyclizing reaction by dehydrochlorination of 3-chloro-1,2-propanediol in an atmosphere of ammonia according to the reaction scheme as described below.

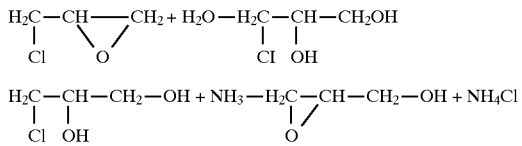

As described hereinabove, in the reaction of glycidol or an epihalohydrin with ammonia, it is thought that a reaction mechanism is a ring-opening addition reaction to epoxy group by attack in which electron pair in the nitrogen atom of ammonia attacks a carbon atom in the epoxy group which is short in electron.

In the reaction, 2-amino-1,3-propanediol which is unpreferred for 1-amino-2,3-propanediol is unavoidably by-produced by a side reaction in which ammonia attacks the second carbon from the terminal without an attack to the carbon at the terminal, and impurities such as bis (2,3-dihydroxypropyl)amine are produced by the reaction of 1-amino-2,3-propanediol with glycidol. It is difficult to avoid the side reaction in view of characteristics in the reaction.

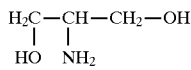

(2-amino-1,3-propanediol)

As described hereinabove, 2-amino-1,3-propanediol is unavoidably by-produced in an amount of 0.3–0.5% by weight based on the weight of 1-amino-2,3-propanediol.

In the second aspect of the present invention, there can be also employed a commercially supplied 1-amino-2,3-propanediol containing approximately 0.3–0.5% by weight of 2-amino-1,3-propanediol as a starting material.

It is difficult to identify 2-amino-1,3-propanediol in 1-amino-2,3-propanediol without a modification because of their similar chemical structure.

Accordingly, 1-amino-2,3-propanediol containing 2-amino-1,3-propanediol is modified by acetylation as being capable of identifying, and a gaschromatographic analysis is carried out, and it is calculated by the ratio of peak area as described below.

$$C_{2\text{-}APD} = \frac{P_{2\text{-}APD} \times 100}{P_{1\text{-}APD}}$$

In the equation, $C_{2\text{-}APD}$ is the concentration of 2-amino-1,3-propanediol, and $P_{1\text{-}APD}$ and $P_{2\text{-}APD}$ are defined as a peak area in relation to 1-amino-2,3-propanediol and 2-amino-1,3-propanediol, respectively, which are obtained in a gaschromatographic analysis after 1-amino-2,3-propanediol is acetylated by an acetylation agent such as trifluoroacetic anhydride.

The gaschromatographic analysis is preferably carried out with the following measurement conditions.

| | |
|---|---|
| Column Packing | ULBON NR-1701 (Fused silica capillary) |
| Column | Length 25 m, Internal diameter 0.2 mm, Film thickness 0.25 microns |
| Column Temperature | Initial 140° C. Final 220° C. Rate of temperature elevation 5° C./minute |
| Detector | Flame ionization detector |
| Injection Temperature | 250° C. |
| Detector Temperature | 250° C. |
| Carrier Gas | Helium |
| Flow Rate | 1.14 ml/minute |
| Split Value | 1:65.14 |
| Sample | 1-amino-2,3-propanediol derivative Sample treated by trifluoroacetic anhydride |
| Sample amount | 1.0 micro liter |
| Range | 10 |
| Calculation | Area percent |

As described hereinabove, 1-amino-2,3-propanediol which is the desired product and 2-amino-1,3-propanediol which is an impure component are very close in their boiling points because of their closely similar chemical structures.

Accordingly, in the case of separating 1-amino-2,3-propanediol from 2-amino-1,3-propanediol with a conventional distillation column, it requires a large amount of theoretical stages, resulting in that a pressure loss in the whole distillation column becomes inevitably large and pressure at column bottom increases.

As described hereinabove, as a result of investigation in the JP-A-04352748 (corresponding to U.S. Pat. No. 5,556, 576 or EP 0470004), it is found that 1-amino-2,3-propanediol can be separated from 2-amino-1,3-propanediol using a distillation column having low pressure loss.

Further, it is also known that 1-amino-2,3-propanediol and high-boiling-point ingredients contained together with 1-amino-2,3-propanediol are thermally stable, resulting in that 1-amino-2,3-propanediol discolors which is a distilled product.

However, the present inventors, as a result of an investigation, found out that 1-amino-2,3-propanediol does not discolor and can be efficiently separated by placing a packing having a low pressure loss per one theoretical plate at both sides of a feeding position of a starting liquid.

The phrase "a distillation column having low pressure loss" described herein means that the pressure loss per one theoretical plate is low, and does not refer to "a pressure loss per a specified height", such as, for example, one meter. It is to be noted that a distillation column having "low pressure loss" in the present invention is preferably a distillation column in which the "low pressure loss per one theoretical plate" is, more specifically, not more than 0.5 Torr. Usually, a pressure loss can readily be measured as "a pressure loss per a unit height" in the case of a distillation column.

Accordingly, it is required to determine "the number of theoretical plates per a unit height" in order to calculate "pressure loss per one theoretical plate" which is a definition in relation to pressure loss of a distillation column to be used in the present invention.

The number of theoretical plates per a unit height can be readily calculated by Fenske's equation [(Kagaku Kogaku Benran, 4th edition), page 598, 1978, published by Maruzen, Ltd. in Japan].

For example, it can be readily calculated by the data obtained from total reflux test using two components in which the relative volatility is nearly constant over a wide range of compositions, that is, it is a nearly ideal system (e.g., chlorobenzene/ethylbenzeneortrans-decalin/cis-decalin, etc.).

Such the distillation column having "low pressure loss per one theoretical plate" can be specifically obtained by using a typical packing described below.

The specific packing includes "Sumitomo/Sulzer Packing BX type or CY type" or "Sumitomo/Sulzer-Labo-Packing", "Sumitomo/Mela Packing" (supplied by Sumitomo Heavy Industries, Ltd.), "Techno Pack 100MD or 50MS" (supplied by Mitsui & Co. Ltd.), and "MC Pack" (supplied by Mitsubishi Shoji, Ltd.) which are supplied on a commercial basis.

All of the above-mentioned packings, which are stacked packings, have pressure loss of not more than 0.5 Torr per one theoretical plate in a conventional range for uses thereof.

On the other hand, in the case of Oldershaw type plate column which is a conventional distillation column, from 2 to 4 actual plates usually correspond to one theoretical plate.

Furthermore, vapor inevitably passes through liquid portion, whereby there is caused a pressure loss corresponding to the liquid height per one actual plate.

On the other hand, pressure loss is low in the case of the packed column, because the packed column does not cause such phenomena.

The above-mentioned packings, which are well-known and commercially available, are designed so that the pressure loss therethrough becomes low.

It is to be noted that stacked packings employed in the packed column are described in detail in, for example, "M. Huber und W. Meier, Sulzer-Kolommen fur Vakuumrektifikation und Stoffaustausch, special print TECHNISCHE RUNDSCHAU SULZER 1/1985", and "Sulzer Brochure, Separation Columns for Distillation and Absorption Packings, Columns, Plants, published 1985".

The required number of total theoretical plates of a distillation column to be used in the present invention varies depending, for example, upon the content of 2-amino-1,3-propanediol in the starting material, the target content of 2-amino-1,3-propanediol in a product, the target yield of 1-amino-2,3-propanediol, and the reflux ratio.

The number of total theoretical plates is usually used in a range of from 3 to 100, and preferably, from 5 to 30.

In the second aspect of the present invention, it is required that the packing having pressure loss of not less than 0.5 Torr must be placed at both sides (an upper side and lower side) of a feeding position for a starting liquid. More specifically, in the above-mentioned theoretical stages, the starting liquid is fed at a position of 2–80 stages of the theoretical stages, and preferably 2–24 stages.

In the case that the feeding position is lower than 2 stages, and when an evaporator is connected to a bottom of the distillation column, 1-amino-2,3-propanediol can not be sufficiently separated from 2-amino-1,3-propanediol because of a small difference in boiling-points thereof, resulting in that 2-amino-1,3-propanediol is distilled out which is a high-boiling-point ingredient and it is mixed into 1-amino-2,3-propanediol which is a desired product.

This depends upon that the packing does not include a collecting portion for 1-amino-2,3-propanediol.

On the other hand, in the case that the feeding position is higher than 80, there increases 2-amino-1,3-propanediol accompanied by 1-amino-2,3-propanediol to be distilled out, resulting in that 2-amino-1,3-propanediol is mixed into 1-amino-2,3-propanediol which is a desired product.

As shown hereinabove, there can be separated 1-amino-2,3-propanediol and 2-amino-1,3-propanediol which have a small difference between their boiling points each other by appropriately adjusting the feeding position into the distillation column in which there is filled a packing having small pressure loss per 1 theoretical stage.

The liquid temperature and pressure in an evaporation vessel which is attached to the bottom of the distillation column, depend, for example, upon the concentration of other components with higher boiling points in a crude 1-amino-2,3-propanediol, the target yield of 1-amino-2,3-propanediol, the number of the theoretical plates of the distillation column, and the pressure loss.

Specifically, the distillation is usually carried out in a liquid temperature range of from 60° to 200° C. and a pressure range of from 0.1 to 30 Torr, in the evaporation vessel.

According to a third aspect of the present invention, there is provided a process for the preparation of a dihydroxyamino compound represented by general formula (1),

(in the formula, $R^1$–$R^7$ are a substituted group which includes any one of a hydrogen atom, an alkyl group, an alkenyl group, and an alkoxy group, respectively) produced by the reaction of an epoxy compound represented by general formula (2),

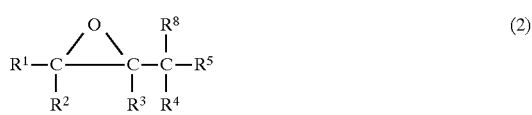

(in the formula, $R^1$–$R^5$ are a substituted group which includes any one of a hydrogen atom, an alkyl group, an alkenyl group, and an alkoxy group, respectively, and $R^8$ is a hydroxyl group or a halogen atom) with an aqueous solution of an amino compound represented by general formula (3),

(in the formula, $R^6$ and $R^7$ are a substituted group which includes any one of a hydrogen atom, an alkyl group, an alkenyl group, and an alkoxy group, respectively), the improvement characterized in that an unreacted amino compound is recollected from a crude reaction solution containing said dihydroxyamino compound and said amino compound as a solution having 5–80% by weight of said amino compound by evaporation, and then said solution is recirculated into a reaction system.

Molar ratio of the above-mentioned amino compound with respect to the above-mentioned epoxy compound is 2–100 mol, and preferably 3–50 mol, based on 1 mol of the epoxy compound in order to improve a yield the dihydroxyamino compound. In the case of less than 2 mol, the yield of the dihydroxyamino compound becomes unpreferably worse, and in the case of exceeding 100 mol, the crude reaction liquid unpreferably increases, space-time-yield unpreferably lowers, water to be removed increases, and the yield of the dihydroxyamino compound does not unpreferably increase compared to the amount of the amino compound.

The amino compound to be fed into a reaction system as a starting raw material is employed as a solution having a concentration of 5–80% by weight, and preferably 10–70% by weight.

In the case that the concentration of the amino compound is less than 5% by weight, the crude reaction liquid unpreferably increases, space-time-yield unpreferably lowers, water to be removed increases, and the yield of the dihydroxyamino compound does not unpreferably increase compared to the amount of the amino compound.

On the other hand, in the case that the concentration of the amino compound exceeds 80% by weight, a boiling point becomes lower in the solution of the amino compound supplied, and a distillate must be cooled in order to recollect as the solution of the amino compound, resulting in that running costs become expensive and an operation in distillation becomes complicated because temperature of a coolant must be lowered.

For example, in the case that the above-mentioned 1-amino-2,3-propanediol is prepared by employing ammonia and glycidol, ammonia is preferably employed as an aqueous solution having approximately 28%.

Further, in the case that the above-mentioned 1-monomethylamino-2,3-propanediol is prepared by employing monomethylamine and glycidol, ammonia is preferably employed as an aqueous solution of monomethylamine having approximately 40%.

A solvent for dissolving the amino compound preferably includes water, methylalcohol, ethylalcohol, propylalcohol, butylalcohol, pentylalcohol, diethylether, dipropylether, and dibutylether. More preferably, there are employed water, methylalcohol, ethylalcohol, propylalcohol, diethylether, dipropylether, and dibutylether.

The reaction is not limited in a style, and there may be employed any one of a continuously streaming type, a batchwise type, and a semi-batch type.

Reaction temperature ranges from −10° to 60° C., preferably from 0° to 50° C. In the temperature range, the dihydroxyamino compound is prepared without causing side reactions between an epoxy compound and an amino compound.

Subsequently, there are evaporated low-boiling-point ingredients such as unreacted amino compound and solvents, etc., from a crude reaction liquid containing the dihydroxyamino compound obtained, unreacted amino compound, and solvents, etc., and the unreacted amino compound and water are recollected at the same time to recirculate into a reaction system.

As an evaporating apparatus, there may unlimitedly be employed a natural circulation evaporator, a forcibly circulation evaporator and a falling liquid-film type evaporator, and in which trays may be equipped at an upper portion of the evaporating apparatus.

In the case that the amino compound has a low boiling point as in ammonia and monomethylamine, and a large difference in boiling points from the dihydroxyamino compound, the amino compound can be recollected as a solution even by equipping a demister for preventing entrainment of mist containing the dihydroxyamino compound.

Even though a small amount of the dihydroxyamino compound is evaporated because of entrainment of mist without equipping the demister, since it is recirculated into the reaction system, a yield does not lower so much.

However, a demister is preferably equipped because of occasional discoloration.

In the evaporation apparatus, the amino compound and solvents in the crude reaction liquid are both evaporated to recollect an amino compound solution. Evaporation style may be continuous or batchwise. In the evaporation apparatus, the amino compound is evaporated from the crude reaction liquid in a concentration of 5–80% by weight, and preferably 10–70% by weight. In the concentration range, the amino compound can be sufficiently employed by recirculation into a reaction system.

For example, in the case that 1-amino-2,3-propanediol is prepared by employing ammonia and glycidol, an ammonia aqueous solution is recollected and recirculated into a reaction system in a concentration of 20–35% by weight, and preferably approximately 28% by weight.

Further, in the case that 1-methylamino-2,3-propanediol is prepared by employing monomethylamine and glycidol, a monomethyl amine aqueous solution is recollected and recirculated into a reaction system in a concentration of 30–50% by weight, and preferably approximately 40% by weight. Concentration of the amino compound evaporated from the evaporation apparatus can be adjusted by changing a evaporation temperature and pressure. The evaporating temperature is different depending upon the composition of the crude reaction liquid.

For example, in the case that ammonia is employed as an amino compound, and water is employed as a solvent, an ammonia aqueous solution is recollected in a concentration of 20–35% by weight, and preferably approximately 28% by weight by heating at 100°–120° C., and preferably 100°–110° C. under ordinary pressures.

Still further, pressures in evaporation is different depending upon a kind of the amino compound and solvent, and evaporation is preferably carried out in a range of 500–1000 Torr, more preferably in a range of 600–900 Torr.

In the case of not more than 500 Torr, boiling point of the amino compound becomes too low, and it becomes unpreferably difficult to recollect the amino compound.

On the other hand, in the case of not less than 1000 Torr, plant costs become expensive.

In the case that temperature for condensing is high in evaporating, the concentration of the amino compound becomes low in an aqueous solution, and contrarily, in the case that temperature for condensing is low in evaporating, the concentration of the amino compound becomes high in an aqueous solution.

In the case that pressure is high in evaporating, the concentration of the amino compound becomes unpreferably high in an aqueous solution, and contrarily, in the case that pressure for condensing is low in evaporating, the concentration of the amino compound becomes unpreferably low in an aqueous solution. For example, in the case that an aqueous ammonia is employed as an amino compound, evaporation is operated in a reflux ratio of not more than 1, preferably not more than 0.5, and usually 0.

In the case that the reflux ratio is large in evaporating, the concentration of the amino compound becomes unpreferably low in an aqueous solution.

For example, since ammonia has a large solubility to water and, whereby, pressure loss is large in a vapor side, there may be preferably employed a liquid-dispersible type condenser having a large area in liquid side. For example, there is exemplified a multi-tube type condenser or a packed column type condenser in which regular-shaped packings (eg. a stacked packing) or irregular-shaped packings are filled.

In order to elevate an efficiency for recollecting the amino compound, a condensed liquid is preferably recirculated into the condenser.

In the third aspect of the present invention, a solution of the amino compound having a desired concentration can be recollected in a 1-stage-evaporation by controlling the temperatures and pressures of the crude reaction liquid in the evaporation apparatus. Liquid containing the dihydroxyamino compound is recollected as a liquid discharged from a bottom of the evaporator.

In the third aspect of the present invention, since the amino compound is removed together with a solvent as a solution, the dihydroxyamino compound having a high concentration can be discharged from a bottom of the evaporator. Subsequently, a dihydroxyamino compound having a high purity is prepared by refining the liquid discharged from a bottom of the evaporator.

According to a fourth aspect of the present invention, there is provided a process for the preparation of a dihydroxyamino compound composed of the steps; distilling a crude liquid in which unreacted amino compound and low-boiling-point ingredients are removed from a crude reaction liquid containing a dihydroxyamino compound represented by general formula (1) produced by the reaction of an epoxy compound represented by general formula (2) with an amino compound represented by general formula (3), and separating the dihydroxyamino compound from high-boiling-point ingredients, the improvement characterized in that said high-boiling-point ingredients are taken out of a bottom of an evaporator in a low concentration state containing not less than 20% by weight of said dihydroxyamino compound, and said dihydroxyamino compound is recollected by distillation with an evaporator,

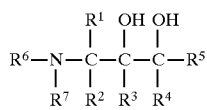 (1)

(in the formula, $R^1$–$R^7$ are a substituted group which includes any one of a hydrogen atom, an alkyl group, an alkenyl group, and an alkoxy group, respectively)

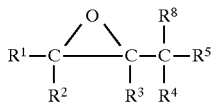 (2)

(in the formula, $R^1$–$R^5$ are a substituted group which includes any one of a hydrogen atom, an alkyl group, an alkenyl group, and an alkoxy group, respectively, and $R^8$ is a hydroxyl group or a halogen atom)

 (3)

(in the formula, $R^6$ and $R^7$ are a substituted group which includes any one of a hydrogen atom, an alkyl group, an alkenyl group, and an alkoxy group, respectively).

In the fourth aspect of the present invention, for example, in the case that ammonia aqueous solution is employed as an amino compound and glycidol is employed as an epoxy compound, and the molar ratio of ammonia with respect to glycidol is approximately 15, 1-amino-2,3-propanediol is present in concentration of approximately 3–10% by weight and unreacted ammonia and water, etc. are present as low-boiling-point ingredients, and further impurities containing bis(2,3-dihydroxypropyl)amine are present as high-boiling-point ingredients in the crude reaction liquid.

The dihydroxyamino compound is preferably contained in concentration of approximately 5–90% by weight, and more preferably approximately 10–70% by weight in a liquid in which there are removed low-boiling-point ingredients such as an excessive amount of the amino compound and solvents from the crude reaction liquid.

In the case that the dihydroxyamino compound is 1-amino-2,3-propanediol, 1-amino-2,3-propanediol is preferably contained in concentration of approximately 30–90% by weight in a crude liquid in which there are removed low-boiling-point ingredients such as an excessive amount of ammonia and water from the crude reaction liquid.

In the crude liquid, there are present impurities containing bis (2,3-dihydroxypropyl)amine and a small amount of low-boiling-point ingredients, etc.

It is to be noted that in the case that concentration of the dihydroxyamino compound in the crude liquid is lower than the above-mentioned lower value, it can be employed in a succeeding step after concentrating by distillation.

As an investigation of a mechanism of discoloration of the dihydroxyamino compound in the succeeding step by the present inventors, it has been found that, for example, in the case of preparing 1-amino-2,3-propanediol as a desired product, it discolors because of formation of discoloring low-boiling-point ingredients through decomposition of 1-amino-2,3-propanediol and bis(2,3-dihydroxypropyl)amine which are high-boiling-point ingredients in a distillation column itself or an evaporator, in which the crude liquid is distilled to separate the dihydroxyamino compound which is a distillate from high-boiling-point ingredients which are a liquid discharged from the evaporator.

The above-mentioned succeeding step is occasionally called as "a product-manufacturing step" in which a purified dihydroxyamino compound is obtained as a final product.

In the case that a distillation apparatus composed of an evaporating portion (an evaporator) and a distillation column is employed in order to separate the dihydroxyamino compound from the crude liquid in which there are removed low-boiling-point ingredients such as an excessive amount of ammonia and water from the crude reaction liquid, internal temperature in the evaporating portion (an evaporator) is preferably 60°–200° C., and more preferably 70°–190° C. In the case that the internal temperature in the evaporating portion (an evaporator) is less than 60° C., viscosity is too high in the crude liquid, unpreferably resulting in that an operation in distillation occasionally becomes difficult.

On the other hand, in the case of exceeding 200° C., the final product which is a distillate is readily discolors because of thermal decomposition, and it unpreferably requires a heating means being capable of supplying high temperature.

Pressure in the evaporator is preferably 0.1–50 Torr, and more preferably 0.5–40 Torr.

In the case that the pressure is less than 0.1 Torr, it unpreferably requires a high price vacuum unit in order to maintain a super high vacuum state.

On the other hand, in the case of exceeding 50 Torr, temperatures elevate in the evaporator because of too high pressures, whereby, the dihydroxyamino compound readily cause thermal deterioration, unpreferably resulting in accelerating discoloration of the dihydroxyamino compound by decomposition.

In the present invention, distillation apparatuses employed for separating the dihydroxyamino compound which is a product from impurities having high-boiling-points are not particularly limited in a style if deterioration by heating can be prevented, and there can be usually employed a distillation apparatus composed of an evaporating portion (an evaporator) and a distillation column.

In the fourth aspect of the present invention, concentration of the dihydroxyamino compound discharged from the evaporator in distillation essentially requires not less than 20% by weight, and preferably not less than 40% by weight.

Into the distillation column, there is supplied the crude liquid in which there are removed having low-boiling-point ingredients such as an excessive amount of ammonia and water from the crude reaction liquid, and there is distilled out a vapor primarily containing the dihydroxyamino compound such as 1-amino-2,3-propanediol as a final product in the "a product-manufacturing step".

A liquid in the evaporator separated from the vapor still contains a relatively fairly amount of the dihydroxyamino compound such as 1-amino-2,3-propanediol.

Accordingly, the dihydroxyamino compound such as 1-amino-2,3-propanediol is further distilled from the liquid in the evaporator using another distillation apparatus, and it is recirculated into the distillation column together with the crude liquid in which there are removed low-boiling-point ingredients such as an excessive amount of ammonia and water from the crude reaction liquid, whereby, there can be decreased loss of the dihydroxyamino compound such as 1-amino-2,3-propanediol. In the case of recirculating, it is preferably supplied into the distillation column after mixed with the crude liquid.

Reasons are as follows.

Although the dihydroxyamino compound such as 1-amino-2,3-propanediol is dissolved in water, since it is not momentarily dissolved because of high viscosity, in the case that it is mixed with the crude reaction liquid containing a large amount of water, a two layers liquid or uneven liquid is occasionally formed without being mixed with each other.

Since the dihydroxyamino compound such as 1-amino-2,3-propanediol to be recirculated only contains an exceedingly small amount of impurities such as bis(2,3-dihydroxypropyl)amine, the impurities are not accumulated in the distillation column.

As described above, discoloration and in the dihydroxyamino compound such as 1-amino-2,3-propanediol which is a final product can be prevented and a yield can be improved by remaining and recirculating a certain amount of the dihydroxyamino compound such as 1-amino-2,3-propanediol in the liquid discharged from the evaporator in the "a product-manufacturing step".

The dihydroxyamino compound such as 1-amino-2,3-propanediol obtained in the fourth aspect of the present invention shows an APHA value of not more than 50, preferably not more than 45, and more preferably not more than 40.

The APHA value enables to improve a yield in a succeeding step such as a process for preparation of an X-ray contrast agent.

In the case of distilling high-boiling-point ingredients in the liquid discharged from the evaporator in the "a product-manufacturing step", for example, when the dihydroxyamino compound such as 1-amino-2,3-propanediol is recollected with an evaporation apparatus equipped with a distilling portion, it discolors and a yield lowers, unpreferably resulting in not being practical.

On the other hand, when the dihydroxyamino compound such as 1-amino-2,3-propanediol is recollected with an evaporation apparatus not equipped with a distilling portion, it does not discolors, a yield is largely improved, and high-boiling-point ingredients can be also condensed in a high concentration, preferably resulting in being practical.

The following Examples are given to illustrate the practice of this invention but they are not intended in any way to act to limit the scope of the invention.

[EXAMPLE 1]

A 5-liter glass-made separable reaction vessel equipped with an agitator and a jacket was charged with 2200 g of ammonia aqueous solution having 28% by weight, followed by feeding 182 g of glycidol over 6 hours, and aging for 3 hours. Reaction temperature was controlled at 15° C.

Concentration of ammonia and water in thus-obtained crude reaction liquid was 24.4% by weight and 66.5% by weight, respectively.

The crude reaction liquid was fed into an apparatus (column size: 40 mm phi×1200 mm H) equipped with a demister at an upper portion of a stainless-made falling-liquid-film-evaporator in feeding speed of 1600 g/hour, and evaporation was carried out in column-top pressure of 760 Torr while heating at 106° C.

A liquid discharged from the evaporator was fed into a distillation apparatus composed of a vacuum-jacket-type packed column (50 mm phi×110 mm H) in which a stacked packing (Sulzer Labo Packing manufactured by Sumitomo Heavy Industry, Ltd. having a specific area of 1700 $m^2/m^3$) is filled and a stainless-made falling-liquid-film evaporator. Distillation was carried out at temperature of 152° C. in an evaporating portion and column-top pressure of 20 Torr to remove residual ammonia and water.

A crude liquid obtained contained 72.0% by weight of 1-amino-2,3-propanediol, 0.9% by weight of water, and 27.1% by weight of other ingredients.

The crude liquid was fed into a distillation apparatus composed of an agitating-type liquid-film evaporator equipped with a steam heating portion by a stainless-made jacket and a vacuum-jacket-type packed column (50 mm phi×385 mm H) in which a stacked packing (Sulzer Labo Packing manufactured by Sumitomo Heavy Industry, Ltd. having a specific area of 1700 $m^2/m^3$) is filled, in feeding speed of 300 g/hour.

Distillation was carried out at temperature of 165° C. and pressure of 5 Torr at an evaporating portion, column-top pressure of 2 Torr and the temperature of 165° C. in the packed column top, and reflux ratio of 1. Vapor distilled out was introduced into a condenser to obtain a condensate at the temperature of 100° C.

It is to be noted that steam pressure which is supplied into the jacket of the evaporating portion was controlled so that a yield of 1-amino-2,3-propanediol is adjusted to 95%. In the condensate obtained, color hue (APHA) was 20, water content was 0.06% by weight, and 1-amino-2,3-propanediol content was 99.5% by weight. Results are shown in Table 1.

[EXAMPLE 2]

The same procedures were followed as in Example 1, except that temperature in the condenser was changed to 120° C. Results are shown in Table 1.

[EXAMPLE 3]

The same procedures were followed as in Example 1, except that temperature in the condenser was changed to 80° C. Results are shown in Table 1.

[Comparative Example 1]

The same procedures were followed as in Example 1, except that temperature in the condenser was changed to 30° C. Results are shown in Table 1.

[Comparative Example 2]

The same procedures were followed as in Example 1, except that column-top pressure was changed to 40 Torr, and temperature in the condenser was changed to 185° C. Results are shown in Table 1.

[EXAMPLE 4]

A 20-liter SUS316-made reaction vessel equipped with an agitator and a jacket was charged with 1711 g of monomethylamine aqueous solution having 40% by weight, followed by feeding 163 g of glycidol over 3 hours, and aging for 1 hour. Reaction temperature was controlled at 30° C.

Concentration of monomethylamine and water in thus-obtained crude reaction liquid was 32% by weight and 54% by weight, respectively.

The crude reaction liquid was fed into an apparatus (column size: 25 mm phi×900 mm H) equipped with a demister at an upper portion of a stainless-made falling-liquid film evaporator in feeding speed of 783 g/hour, and evaporation was carried in column-top pressure of 760 Torr while heating at 105° C. to remove unreacted monomethylamine and water and to obtain a crude liquid.

In the crude liquid obtained, 1-monomethylamino-2,3-propanediol content was 73.4% by weight, water content was 0.6% by weight, and other ingredients were 26.0% by weight.

The crude liquid was fed into the same distillation apparatus as in Example 1 in feeding speed of 300 g/hour, and distillation was carried out at temperature of 160° C. and pressure of 7.0 Torr at an evaporating portion, column-top pressure of 3.6 Torr and the temperature of 120° C. in the packed column top, and reflux ratio of 2. Vapor distilled out was introduced into a condenser to obtain a condensate at the temperature of 100° C.

It is to be noted that steam pressure which is supplied into the jacket of the evaporating portion was controlled so that a yield of 1-monomethylamino-2,3-propanediol (1-MAPD) is adjusted to 95%. In the condensate obtained, color hue (APHA) was 20, water content was 0.04% by weight, and 1-monomethylamino-2,3-propanediol content was 99.4% by weight. Results are shown in Table 2.

[EXAMPLE 5]

The same procedures were followed as in Example 4, except that temperature in the condenser was changed to 80° C. Results are shown in Table 2.

[Comparative Example 4]

The same procedures were followed as in Example 4, except that temperature in the condenser was changed to 185° C. Results are shown in Table 2.

TABLE 1

| | Temperature (°C.) | | Pressure (Torr) | | Temperature in condenser (°C.) | Yeild (%) | Color (APHA) | Content (wt %) | |
|---|---|---|---|---|---|---|---|---|---|
| | Evaporating portion | Distillation column | Evaporating portion | Distillation column | | | | Water | 1-APD |
| Example 1 | 165 | 130 | 5 | 2 | 100 | 95.0 | 20 | 0.06 | 99.5 |
| 2 | 168 | 130 | 5 | 2 | 120 | 94.7 | 20 | 0.05 | 99.5 |
| 3 | 170 | 131 | 5 | 2 | 80 | 94.4 | 30 | 0.15 | 99.2 |
| Comparative | | | | | | | | | |
| Example 1 | 170 | 130 | 5 | 2 | 30 | 94.6 | 70 | 0.33 | 99.0 |
| 2 | 200 | 186 | 46 | 40 | 185 | 90.6 | 80 | 0.03 | 99.1 |

1-APD: 1-amino-2,3-propanediol

TABLE 2

|  | Temperature (°C.) | | Pressure (Torr) | | Temperature in condenser (°C.) | Yeild (%) | Color (APHA) | Content (wt %) | |
|---|---|---|---|---|---|---|---|---|---|
|  | Evaporating portion | Distillation column | Evaporating portion | Distillation column | | | | Water | 1-MAPD |
| Example 4 | 160 | 120 | 7.0 | 3.6 | 100 | 95.0 | 20 | 0.04 | 99.4 |
| 5 Comparative | 162 | 119 | 6.8 | 3.6 | 80 | 94.4 | 20 | 0.11 | 99.2 |
| Example 3 | 161 | 119 | 7.0 | 3.6 | 30 | 94.2 | 70 | 0.31 | 98.8 |
| 4 | 210 | 165 | 43.0 | 40.0 | 185 | 92.7 | 80 | 0.05 | 99.0 |

1-MAPD: 1-monomethylamino-2,3-propanediol

[Example 6]

A 20-liter SUS316-made reaction vessel equipped with an agitator and a jacket was charged with 1600 g of monoethylamine aqueous solution having 70% by weight, followed by feeding 180 g of glycidol over 4 hours, and aging for 1 hour. Reaction temperature was controlled at 30° C.

Concentration of monoethylamine and water in thus-obtained crude reaction liquid was 53.5% by weight and 26.0% by weight, respectively.

The crude reaction liquid was fed into an apparatus (column size: 25 mm phi×900 mm H) equipped with a demister at an upper portion of a stainless-made falling-liquid film evaporator in feeding speed of 500 g/hour, and evaporation was carried out in column-top pressure of 760 Torr while heating at 102° C.

Subsequently, a crude liquid discharged from the evaporator was introduced into the same distillation apparatus as in Example 1, followed by distilling at temperature of evaporating portion of 133° C. and in column-top pressure of 200 Torr to remove unreacted monoethylamine and water and to obtain a crude liquid.

In the crude liquid, 1-monoethylamino-2,3-propanediol content was 80.4% by weight, water content was 1.0% by weight, and other ingredients content was 19.0% by weight.

Subsequently, the crude liquid was fed into the same distillation apparatus as in Example 1 in feeding speed of 300 g/hour, and distillation was carried out at the temperature of 165° C. and pressure of 7.1 Torr at an evaporating portion, column-top pressure of 3.6 Torr and the temperature of 125° C. in the packed column top, and reflux ratio of 2. Vapor distilled out was introduced into a condenser to obtain a condensate at the temperature of 80° C.

It is to be noted that steam pressure which is supplied into the jacket of the evaporating portion was controlled so that a yield of 1-monoethylamino-2,3-propanediol is adjusted to 95%. In the condensate obtained, color hue (APHA) was 10, water content was 0.07% by weight, and 1-monoethylamino-2,3-propanediol content was 99.6% by weight. Results are shown in Table 3.

[Comparative Example 5]

The same procedures were followed as in Example 6, except that temperature in the condenser was changed to 10° C. Results are shown in Table 3.

TABLE 3

|  | Temperature (°C.) | | Pressure (Torr) | | Temperature in condenser (°C.) | Yeild (%) | Color (APHA) | Content (wt %) | |
|---|---|---|---|---|---|---|---|---|---|
|  | Evaporating portion | Distillation column | Evaporating portion | Distillation column | | | | Water | 1-EAPD |
| Example 6 | 165 | 125 | 7.1 | 3.6 | 80 | 95.0 | 10 | 0.04 | 99.6 |
| Comparative Example 5 | 164 | 125 | 7.0 | 3.6 | 10 | 93.7 | 60 | 0.56 | 99.0 |

1-EAPD: 1-monomethylamino-2,3-propanediol

According to the first aspect of the present invention, there can be provided a process for the preparation of a dihydroxyamino compound in which water and discoloring ingredients are removed while preventing decomposition thereof by distilling a reaction crude liquid at a specified temperature and pressure.

[EXAMPLE 7]

A 5-liter glass-made separable reaction vessel equipped with an agitator and a jacket was charged with 2200 g of ammonia aqueous solution having 28% by weight, followed by feeding 182 g of glycidol over 6 hours, and aging for 3 hours. Reaction temperature was controlled at 15° C.

Concentration of 1-amino-2,3-propanediol in thus-obtained crude reaction liquid was 6.5% by weight.

The crude reaction liquid was fed into an apparatus (column size: 40 mm phi×1200 mm H) equipped with a demister at an upper portion of a stainless-made falling-liquid film evaporator in feeding speed of 1600 g/hour, and evaporation was carried out in column-top pressure of 760 Torr while heating at 106° C.

A crude liquid discharged from the evaporator was fed into a distillation apparatus composed of a vacuum jacket type packed column (50 mm phi×110 mm H) in which a stacked packing (Sulzer Labo Packing manufactured by Sumitomo Heavy Industry, Ltd. having a specific area of 1700 m²/m³) is filled and a stainless-made falling-liquid film evaporator. Distillation was carried out at temperature of 152° C. in an evaporating portion and column-top pressure of 20 Torr to remove residual ammonia and water.

Thus-obtained crude liquid contained 72.0% by weight of 1-amino-2,3-propanediol, 0.9% by weight of water, and 27.1% by weight of other ingredients.

The crude liquid was fed into a distillation apparatus (a product-manufacturing step) composed of an agitating-type liquid film evaporator equipped with a steam heating portion by a stainless-made jacket and a vacuum-jacket type packed column (50 mm phi×385 mm H) in which a stacked packing (Sulzer Labo Packing manufactured by Sumitomo Heavy Industry, Ltd. having a specific area of 1700 m²/m³) is filled, in feeding speed of 300 g/hour.

Distillation was carried out at the temperature of 165° C. and pressure of 5 Torr at an evaporating portion, column-top pressure of 2 Torr and the temperature of 165° C. in the packed column top, and reflux ratio of 1. Feeding position was a position of 275 mm H (the height of approximately 71% from a bottom of the stacked packing) from a bottom of the packed column.

It is to be noted that steam pressure which is supplied into the jacket of the evaporating portion was controlled so that concentration of 1-amino-2,3-propanediol is adjusted to 40%. In a product obtained, 1-amino-2,3-propanediol content was 99.5% by weight. Results are shown in Table 4.

[Comparative Example 6]

The same procedures were followed as in Example 7, except that feeding position is the bottom of the packed column in the product-manufacturing step. Results are shown in Table 4.

[EXAMPLE 8]

The same procedures were followed as in Example 7, except that the feeding position is 330 mm H (the height of approximately 86% from a bottom of the stacked packing) from the bottom of the packed column in the product-manufacturing step. Results are shown in Table 4.

[EXAMPLE 9]

The same procedures were followed as in Example 7, except that there was employed a commercially supplied 1-amino-2,3-propanediol in the product-manufacturing step.

Results are shown in Table 4.

[EXAMPLE 10]

The same procedures were followed as in Example 7, except that the feeding position is 165 mm H (the height of approximately 43% from a bottom of the stacked packing) from the bottom of the packed column in the product-manufacturing step. Results are shown in Table 4.

[EXAMPLE 11]

The same procedures were followed as in Example 7, except that the feeding position is 110 mm H (the height of approximately 29% from a bottom of the stacked packing) from the bottom of the packed column in the product-manufacturing step. Results are shown in Table 4.

Results are shown in Table 4.

TABLE 4

| | A | B | theoretical plate number | pressure at column-top (Torr) | feeding position (mm H) | yield (%) | G | H |
|---|---|---|---|---|---|---|---|---|
| Example 7 | 72.0 | 0.4 | 5 | 3 | 275 | 85 | 0.20 | 45 |
| Comparative Example 6 | 72.0 | 0.4 | 5 | 3 | 0 | 81 | 0.43 | 45 |
| Example 8 | 72.0 | 0.4 | 5 | 3 | 380 | 84 | 0.31 | 50 |
| 9 | 99.4 | 0.4 | 5 | 3 | 275 | 96 | 0.19 | 25 |
| 10 | 72.0 | 0.4 | 5 | 3 | 165 | 85 | 0.25 | 40 |
| 11 | 72.0 | 0.4 | 5 | 3 | 110 | 84 | 0.29 | 45 |

In the Table 4, the alphabets A–H are as follows.
A: 1-amino-2,3-propanediol content (% by weight) in a liquid fed into the product-manufacturing step
B: 2-amino-1,3-propanediol content (% by weight) in a liquid fed into the product-manufacturing step
G: 1-amino-2,3-propanediol content (% by weight) in a liquid (a product) discharged from the product-manufacturing step
H: 2-amino-1,3-propanediol content (% by weight) in a liquid (a product) discharged from the product-manufacturing step As described hereinabove, in the case that a dihydroxyamino compound such as 1-amino-2,3-propanediol is prepared from an epoxy compound such as glycidol or an epihalohydrin and an amino compound such as ammonia, and there is refined a crude reaction liquid containing the dihydroxyamino compound such as 1-amino-2,3-propanediol and a small amount of by-produced impurities such as 2-amino-1,3-propanediol by distillation, the dihydroxyamino compound having a high purity can be obtained by feeding the crude liquid between packings having low pressure loss in the product-manufacturing step.

[EXAMPLE 12]

A 5-liter glass made separable reaction vessel equipped with an agitator and a jacket was charged with 2200 g of ammonia aqueous solution having 28% by weight, followed by feeding 182 g of glycidol over 6 hours, and aging for 3 hours. Reaction temperature was controlled at 15° C.

Concentration of ammonia and water in thus-obtained crude reaction liquid was 24.4% by weight and 66.5% by weight, respectively.

The crude reaction liquid was fed into an apparatus (column size: 25 mm phi×900 mm H) equipped with a demister at an upper portion of a stainless-made falling film evaporator in feeding speed of 608 g/hour, and evaporation was carried out in column-top pressure of 760 Torr while heating at 103° C.

Concentration of ammonia in a distillate (ammonia aqueous solution) was 27.9% by weight, and it was able to recollect ammonia with a recollecting ratio of 99% together with obtaining 1-amino-2,3-propanediol having a high purity and a low color hue.

[Comparative Example 7]

Ammonia was recollected by feeding the crude reaction liquid obtained in Example 12 into a pressurized distillation column (distilling portion: 40 mm phi×1200 mm H) equipped with total stages of 40 with feeding speed of 1600 g/hour. In order to recollect 97% of ammonia, there required column-top pressure of 4408 Torr and heating temperature of 160° C.

[EXAMPLE 13]

A 20-liter SUS316-made reaction vessel equipped with an agitator and a jacket was charged with 1711 g of monomethylamine aqueous solution having 40% by weight, followed by feeding 163 g of glycidol over 3 hours, and aging for 1 hour. Reaction temperature was controlled at 30° C.

Concentration of monomethylamine and water in thus-obtained crude reaction liquid was 32% by weight and 54% by weight, respectively.

The crude reaction liquid was fed into an apparatus (column size: 25 mm phi×900 mm H) equipped with a demister at an upper portion of a stainless-made falling-liquid film evaporator in feeding speed of 783 g/hour, and evaporation was carried in column-top pressure of 760 Torr while heating at 105° C.

Concentration of monomethylamine in a distillate (a monomethylamine aqueous solution) was 39.8% by weight, and it was able to recollect and recirculate monomethylamine with a recollecting ratio of 99% together with obtaining 1-monomethylamino-2,3-propanediol having a high purity and a low color hue.

As described hereinabove, according to the third aspect of the present invention, an amino compound such as ammonia or monomethylamine can be recollected with a high recollecting ratio as an aqueous solution together with obtaining a dihydroxyamino compound such as 1-amino-2,3-propanediol and 1-monomethylamino-2,3-propanediol having a high purity.

[EXAMPLE 14]

A 5-liter glass made separable reaction vessel equipped with an agitator and a jacket was charged with 2200 g of ammonia aqueous solution having 28% by weight, followed by feeding 182 g of glycidol over 6 hours, and aging for 3 hours. Reaction temperature was controlled at 15° C.

Concentration of 1-amino-2,3-propanediol in thus-obtained crude reaction liquid was 6.5% by weight.

The crude reaction liquid was fed into an apparatus (column size: 40 mm phi×1200 mm H) equipped with a demister at an upper portion of a stainless-made falling-liquid film evaporator in feeding speed of 1600 g/hour, and evaporation was conducted in column-top pressure of 760 Torr while heating at 106° C. A liquid discharged from the evaporator was fed into a distillation apparatus composed of a vacuum-jacket type packed column (50 mm phi×110 mm H) in which a stacked packing (Sulzer Labo Packing manufactured by Sumitomo Heavy Industry, Ltd. having a specific area of 1700 m²/m³) is filled and a stainless-made falling film evaporator.

Distillation was carried out at temperature of 152° C. in an evaporating portion and column-top pressure of 20 Torr to remove residual ammonia and water.

A crude liquid obtained in which low-boiling-points ingredients such as unreacted ammonia and water are removed contained 72.0% by weight of 1-amino-2,3-propanediol, 0.9% by weight of water, and 27.1% by weight of other ingredients.

Subsequently, the crude liquid was fed into a distillation apparatus composed of an agitating type liquid film evaporator equipped with a steam heating portion by a stainless-made jacket and a distillation apparatus equipped with a vacuum jacketed packed column (50 mm phi×385 mm H) in which a stacked packing (Sulzer Labo Packing manufactured by Sumitomo Heavy Industry, Ltd. having a specific area of 1700 m²/m³) is filled, in feeding speed of 300 g/hour. Distillation was carried out at column-top pressure of 2 Torr in the packed column top and ref lux ratio of 1 while maintaining temperature at evaporating portion constant in order to adjust the concentration of 1-amino-2,3-propanediol in a liquid from discharged from the evaporator to 40% by weight.

The liquid from discharged from the evaporator was fed into an agitating type liquid film evaporator equipped with a steam heating portion by a stainless-made jacket in feeding speed of 135.5 g/hour to obtain a distillate containing 1-amino-2,3-propanediol of 90% by weight in 53 g/hour.

The distillate was mixed with the above-mentioned crude liquid in which low-boiling-point ingredients such as unreacted ammonia and water in a mixing ratio of 300/53, and a mixture was distilled again with a distillation apparatus (a product-manufacturing column) equipped with a demister at an upper portion of a stainless-made agitating film evaporator in feeding speed of 353 g/hour. Distillation was carried out at column-top pressure of 2 Torr in the packed column top and ref lux ratio of 1 while maintaining temperature at evaporating portion constant in order to adjust the concentration of 1-amino-2,3-propanediol in a liquid from discharged from the evaporator to 40% by weight APHA was 40 in thus-obtained distillate which is a product, and loss was 3% in a product manufacturing step.

Results are shown in Table 5.

[Comparative Example 8]

The same procedures were followed as in Example 14, except that there was adjusted the concentration of 1-amino-2,3-propanediol in a liquid from discharged from the evaporator to 7% by weight, and the liquid was not distilled again. Results are shown in Table 5.

[Comparative Example 9]

The same procedures were followed as in Example 14, except that there was adjusted the concentration of 1-amino-2,3-propanediol in a liquid from discharged from the evaporator to 15% by weight, and the liquid was not distilled again. Results are shown in Table 5.

TABLE 5

| | PMC | | | LDFE | | |
|---|---|---|---|---|---|---|
| | CPT (Torr) | CTT (°C.) | EBT (°C.) | 1-APDC (wt %) | LR (wt %) | CH (APHA) |
| Example 14 | 5 | 130 | 150 | 40 | 3 | 40 |
| Comparative Example | | | | | | |
| 8 | 5 | 128 | 190 | 7 | 9 | 70 |
| 9 | 5 | 131 | 175 | 15 | 6 | 60 |

In the Table 5, abbreviations are as follows.
PMC: Column in the product-manufacturing step
CTP: Column-top pressure (Torr)
CTT: Column-top temperature
EBT: Evaporator-bottom temperature (° C.)
LDFE: Liquid discharged from Evaporator
1-APDC: Concentration of 1-amino-2,3-propanediol (% by weight)
LR: Loss ratio (% by weight)
CH: Color hue (APHA)

While the invention has been described in detail and with reference to specific embodiments thereof, it will be apparent to one skilled in the art that various changes and modifications can be made therein without departing from a spirit and scope thereof.

What is claimed is:

1. A process for the preparation of a dihydroxyamino compound characterized in that a crude reaction liquid containing a dihydroxyamino compound represented by general formula (1);

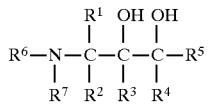   (1)

in which $R^1$–$R^7$ are each independently a hydrogen atom, an alkyl group, an alkenyl group or an alkoxy group, respectively is distilled in a column-top pressure of 0.1–30 torr and a temperature of 60°–200° C., and then distilled vapor is cooled at a temperature of 40°–180° C., said dihydroxyamino compound is separated from water and low-boiling-point ingredients, and water content is adjusted to not more than 0.2% in said dihydroxyamino compound.

2. A process for the preparation of a dihydroxyamino compound as set forth in claim 1, wherein said crude reaction liquid contains a dihydroxyamino compound produced by a reaction of an epoxy compound represented by general formula (2);

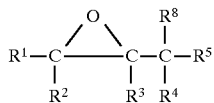   (2)

in which $R^1$–$R^5$ are each independently a hydrogen atom, an alkyl group, an alkenyl group or an alkoxy group, respectively, and $R^8$ is a hydroxyl group or a halogen atom with an amino compound represented by general formula (3);

   (3)

in which $R^6$ and $R^7$ are each independently a hydrogen atom, an alkyl group, an alkenyl group or an alkoxy group, respectively.

3. A process for the preparation of a dihydroxyamino compound as set forth in any one of claim 1 or 2, wherein said dihydroxyamino compound is 1-amino-2,3-propanediol.

4. A process for the preparation of a dihydroxyamino compound as set forth in any one of claim 1 or 2, wherein said dihydroxyamino compound is 1-monomethylamino-2,3-propanediol.

5. A process for the preparation of 1-amino-2,3-propanediol characterized in that there is employed a distillation column equipped with a packing having pressure loss of not more than 0.5 torr per 1 theoretical plate at an upper side and a lower side of a feeding position, in the case that 1-amino-2,3-propanediol is obtained as a distillate by separation of a mixed liquid primarily containing 1-amino-2,3-propanediol and containing 2-amino-1,3-propanediol which is a by-product, water, and high-boiling-point ingredients with a distillation column.

6. A process for the preparation of 1-amino-2,3-propanediol as set forth in claim 5, wherein said mixed liquid is a crude reaction liquid obtained in a reaction of ammonia with glycidol or an epihalohydrin.

7. A process for the preparation of 1-amino-2,3-propanediol as set forth in claim 5 or 6, wherein the weight proportion of 1-amino-2,3-propanediol with respect to 2-amino-1,3-propanediol is 99.5/0.5–99.7/0.3 in said mixed liquid.

8. A process for the preparation of 1-amino-2,3-propanediol as set forth in claim 5, wherein said packing is a stacked packing.

9. A process for the preparation of a dihydroxyamino compound represented by general formula (1),

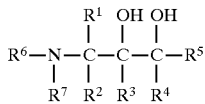   (1)

in which $R^1$–$R^7$ are each independently a hydrogen atom, an alkyl group, an alkenyl group or an alkoxy group, respectively produced by the reaction of an epoxy compound represented by general formula (2),

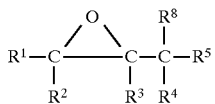   (2)

in which $R^1$–$R^5$ are each independently a hydrogen atom, an alkyl group, an alkenyl group or an alkoxy group, respectively, and $R^8$ is a hydroxyl group or a halogen atom with an aqueous solution of an amino compound represented by general formula (3),

   (3)

in which $R^6$ and $R^7$ are each independently a hydrogen atom, an alkyl group, an alkenyl group or an alkoxy group, respectively, the improvement characterized in that an unreacted amino compound of formula (3) is recollected from a crude reaction solution containing said dihydroxyamino compound and said amino compound as a solution containing 5–80% by weight of said amino compound by evaporation, and then said solution is recirculated into a reaction system.

10. A process for the preparation of a dihydroxyamino compound represented by the general formula (1) as set forth in claim 9, wherein said evaporation is carried out in a temperature of 70°–150° C. and a pressure of 50–1000 torr.

11. A process for the preparation of a dihydroxyamino compound represented by the general formula (1) as set forth in claim 9, wherein said amino compound represented by the general formula (3) is ammonia, said epoxy compound represented by the general formula (2) is glycidol or an epihalohydrin, and said dihydroxyamino compound represented by the general formula (1) is 1-amino-2,3-propanediol.

12. A process for the preparation of a dihydroxyamino compound represented by the general formula (1) as set forth in claim 9, wherein said amino compound represented by the general formula (3) is monomethylamine, said epoxy compound represented by the general formula (2) is glycidol or an epihalohydrin, and said dihydroxyamino compound represented by the general formula (1) is 1-monomethylamino-2,3-propanediol.

13. A process for the preparation of a dihydroxyamino compound represented by the general formula (1) as set forth in claim 9, wherein said evaporation is carried out in reflux ratio of not more than 1.

14. A process for the preparation of a dihydroxyamino compound represented by the general formula (1) as set forth in claim 9, wherein said evaporation is carried out with an evaporator in which a demister is equipped.

15. A process for the preparation of a dihydroxyamino compound represented by the general formula (1) as set forth in claim 9, wherein said solution is recollected as an ammonia aqueous solution having a concentration of 20–35% by weight.

16. In a process for the preparation of a dihydroxyamino compound comprising the steps of distilling a crude liquid in which an unreacted amino compound and low-boiling-point ingredients are removed from a crude reaction liquid containing a dihydroxyamino compound represented by general formula (1) produced by the reaction of an epoxy compound represented by general formula (2) with an amino compound represented by general formula (3), and separating the dihydroxyamino compound from said low-boiling-point ingredients are taken out of a bottom of an evaporator in a low concentration state containing not less than 20% by weight of said dihydroxyamino compound, and said dihydroxyamino compound is recollected by evaporation with an evaporator, said dihydroxyamino compound having the general formula (1) being

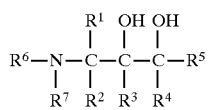  (1)

in which $R^1$–$R^7$ are each independently a hydrogen atom, an alkyl group, an alkenyl group or an alkoxy group, respectively said epoxy compound having the general formula (2) being

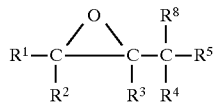  (2)

in which $R^1$–$R^6$ are each independently a hydrogen atom, an alkyl group, an alkenyl group or an alkoxy group, respectively, and $R^8$ is a hydroxyl group or a halogen atom and said amino compound of general formula (3) being

  (3)

in which $R^6$ and $R^7$ are each independently a hydrogen atom, an alkyl group, an alkenyl group or an alkoxy group, respectively.

17. A process for the preparation of a dihydroxyamino compound represented by the general formula (1) as set forth in claim 16, wherein said dihydroxyamino compound recollected from said evaporator is recirculated into a reaction step or a step after removing low-boiling-point ingredients.

18. A process for the preparation of a dihydroxyamino compound represented by the general formula (1) as set forth in claim 16, wherein said evaporation does not include a distilling portion for refining.

19. A process for the preparation of a dihydroxyamino compound represented by the general formula (1) as set forth in claim 16, wherein said amino compound represented by the general formula (3) is ammonia, said epoxy compound represented by the general formula (2) is glycidol or an epihalohydrin, and said dihydroxyamino compound represented by the general formula (1) is 1-amino-2,3-propanediol.

20. A process for the preparation of a dihydroxyamino compound represented by the general formula (1) as set forth in claim 16, wherein said amino compound represented by the general formula (3) is monomethylamine, said epoxy compound represented by the general formula (2) is glycidol or an epihalohydrin, and dihydroxyamino compound represented by the general formula (1) is 1-monomethylamino-2,3-propanediol.

* * * * *